United States Patent [19]

Hill et al.

[11] Patent Number: 5,727,548
[45] Date of Patent: *Mar. 17, 1998

[54] STRIP ELECTRODE WITH SCREEN PRINTING

[75] Inventors: Hugh Allen Oliver Hill, Oxford; Irving John Higgins, Bedford; James Michael McCann, Oxford, all of Great Britain; Graham Davis, Plainsborough, N.J.

[73] Assignee: MediSense, Inc., Bedford, Mass.

[*] Notice: The term of this patent shall not extend beyond the expiration date of Pat. No. 5,509,410.

[21] Appl. No.: 469,205

[22] Filed: Jun. 6, 1995

Related U.S. Application Data

[63] Continuation of Ser. No. 281,237, Jul. 27, 1994, Pat. No. 5,509,410, which is a continuation of Ser. No. 905,504, Jun. 25, 1992, abandoned, which is a continuation of Ser. No. 762,657, Sep. 19, 1991, which is a continuation of Ser. No. 429,055, Oct. 30, 1989, which is a division of Ser. No. 2,120, Jan. 12, 1987, which is a continuation-in-part of Ser. No. 607,599, May 7, 1984, abandoned, which is a continuation-in-part of Ser. No. 590,864, Mar. 19, 1984.

[30] Foreign Application Priority Data

| May 5, 1983 | [GB] | United Kingdom | 8312261 |
| May 5, 1983 | [GB] | United Kingdom | 8312262 |
| Jun. 6, 1983 | [GB] | United Kingdom | 8323799 |
| Dec. 16, 1983 | [GB] | United Kingdom | 8333644 |
| Jan. 11, 1984 | [GB] | United Kingdom | 8400650 |
| Feb. 29, 1984 | [GB] | United Kingdom | 8405262 |
| Feb. 29, 1984 | [GB] | United Kingdom | 8405263 |

[51] Int. Cl.$^6$ ............................................ A61B 5/00
[52] U.S. Cl. ................... 128/637; 128/639; 204/403; 204/407; 204/435
[58] Field of Search ..................... 128/637–642; 204/402, 403, 407, 435

[56] References Cited

U.S. PATENT DOCUMENTS

| 3,352,762 | 11/1967 | Weiner . |
| 3,542,662 | 11/1970 | Hicks et al. . |
| 3,838,033 | 9/1974 | Mindt et al. . |
| 3,900,382 | 8/1975 | Brown, Jr. . |

(List continued on next page.)

FOREIGN PATENT DOCUMENTS

| 030503A1 | 6/1981 | European Pat. Off. . |
| 078636A1 | 5/1983 | European Pat. Off. . |
| 127958A2 | 12/1984 | European Pat. Off. . |
| 152541A1 | 8/1985 | European Pat. Off. . |
| 0351891A2 | 1/1990 | European Pat. Off. . |

(List continued on next page.)

OTHER PUBLICATIONS

Aizawa et al., "Amperometric Determination of Human Gonadotropin by Membrane–Bound Antibody," Enzyme Immunosensor 22–28, 1978.

(List continued on next page.)

*Primary Examiner*—David Shay
*Attorney, Agent, or Firm*—Fish & Richardson P.C.

[57] ABSTRACT

A sensor system that detects a current representative of a compound in a liquid mixture features a two-electrode strip adapted for releasable attachment to signal readout circuitry. The strip comprises an elongated support (preferably flat) adapted for releasable attachment to the readout circuitry; a first conductor and a second conductor each extend along the support and comprise means for connection to the circuitry. An active electrode, positioned to contact the liquid mixture and the first conductor, comprises a single layer deposit of an enzyme capable of catalyzing a reaction involving the compound, a conductive material, and an electron mediator, capable of transferring electrons between the enzyme-catalyzed reaction and the first conductor. A reference electrode is positioned to contact the mixture and the second conductor. The system includes circuitry adapted to provide an electrical signal representative of the current. The two-electrode strip is manufactured, e.g., by screen printing, an admixture of an enzyme a conductive material, and a mediator as a single layer onto the substrate.

8 Claims, 6 Drawing Sheets

U.S. PATENT DOCUMENTS

| | | |
|---|---|---|
| 4,008,717 | 2/1977 | Kowarski . |
| 4,019,966 | 4/1977 | Reimes et al. . |
| 4,068,923 | 1/1978 | Toida . |
| 4,133,735 | 1/1979 | Afromowitz et al. . |
| 4,176,659 | 12/1979 | Rolfe . |
| 4,185,131 | 1/1980 | Goller et al. . |
| 4,216,245 | 8/1980 | Johnson . |
| 4,224,125 | 9/1980 | Nakamura et al. . |
| 4,225,410 | 9/1980 | Pace . |
| 4,229,490 | 10/1980 | Frank et al. . |
| 4,334,542 | 6/1982 | Takinishi et al. . |
| 4,352,884 | 10/1982 | Nakashima et al. . |
| 4,356,074 | 10/1982 | Johnson . |
| 4,376,689 | 3/1983 | Nakamura et al. . |
| 4,390,620 | 6/1983 | Junter et al. . |
| 4,394,070 | 7/1983 | Brown et al. . |
| 4,449,529 | 5/1984 | Burns et al. . |
| 4,454,007 | 6/1984 | Pace . |
| 4,469,110 | 9/1984 | Slama . |
| 4,488,556 | 12/1984 | Ho . |
| 4,490,464 | 12/1984 | Gorton et al. . |
| 4,545,382 | 10/1985 | Higgens et al. . |
| 4,592,824 | 6/1986 | Smith et al. . |
| 4,711,245 | 12/1987 | Higgins et al. . |
| 5,509,410 | 4/1996 | Hill et al. ................................ 128/637 |

FOREIGN PATENT DOCUMENTS

| | | |
|---|---|---|
| 2127142 | 6/1971 | Germany . |
| 54-130196 | 3/1978 | Japan . |
| 60-29658 | 7/1983 | Japan . |
| 61-161443 | 7/1986 | Japan . |
| 61-270652 | 11/1986 | Japan . |
| 827023 | 5/1981 | U.S.S.R. . |
| 1318815 | 5/1973 | United Kingdom . |
| 2175400 | 5/1986 | United Kingdom . |
| WO 84/03562 | 9/1984 | WIPO . |

OTHER PUBLICATIONS

Bertrand et al., "Multipurpose Electrode with Different Enzyme Systems Bound to Collagen Films," Analytics Chemics Acts 126:23–34, 1981.

Brodnick et al., "Laminated Electrodes for Biopotential Studies", IEEE Transactions on Biomedical Engineering BME–25:479–481, 1978.

Hill, "The Exploitation of the Electrochemistry of Proteins", Biochemical Society Transactions 11:453–455 1983.

Koryta et al., "Electroanalytical Methods Used in Medicine and Biology", Medical and Biological Applications of Electrochemical Devices 7–11, 1980.

Liu et al., "Fabrication of Miniature $PO_2$ and pH Sensors Using Microelectronic Techniques", Diabetes Care 5:275–275–277, 1982.

Liu et al., "Miniature Multiple Cathode Dissolved Oxygen Sensor for Marine Science Applications", Marine Technology 16:468–472, 1980.

May et al., "A Tantalum–on–Sapphire Microelectrode Array", IEEE Transactions on Electron Devices ED–26:1932–1939, 1979.

Oehme, "Chemische Sensoren," Vieweg Verlag, p. 76, 1991.

Pickard et al., "Flexible Printed–Circuit Probe for Electrophysiology", Med. & Biol. Eng. & Comput. 17:261–267, 1979.

Turner et al., "Applications of Electron Transfer Between Biological Systems and Electrodes", Biochemical Society Transactions 11:445–448, 1983.

Updike et al., "The Enzyme Electrode", Nature 214:986–988, 1967.

Technical Note — "A Microelectrode Amplifier with Novel Frequency Compensation", Med. & Biol. Engng. 9:557–561, 1971.

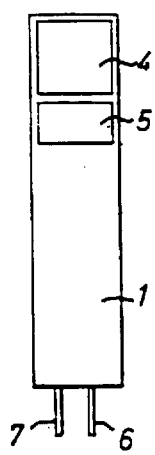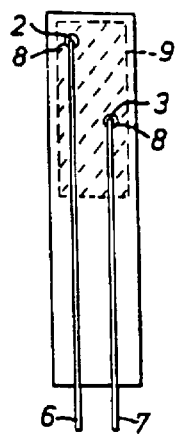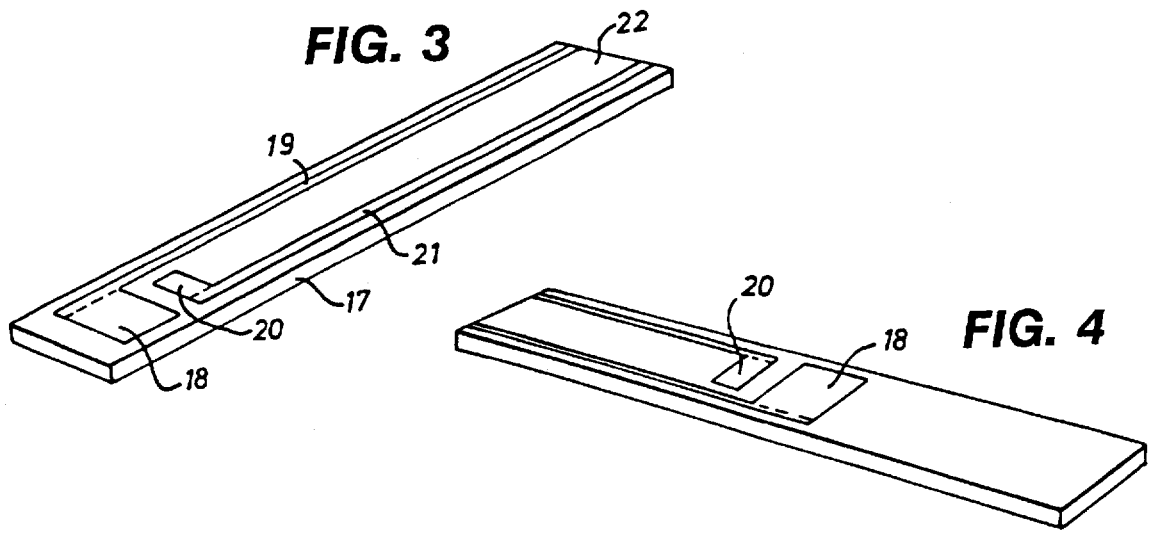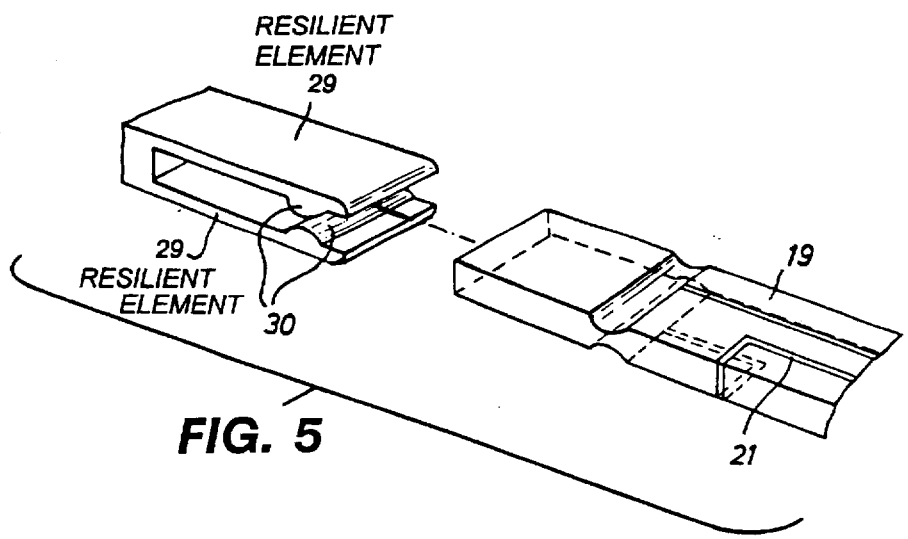

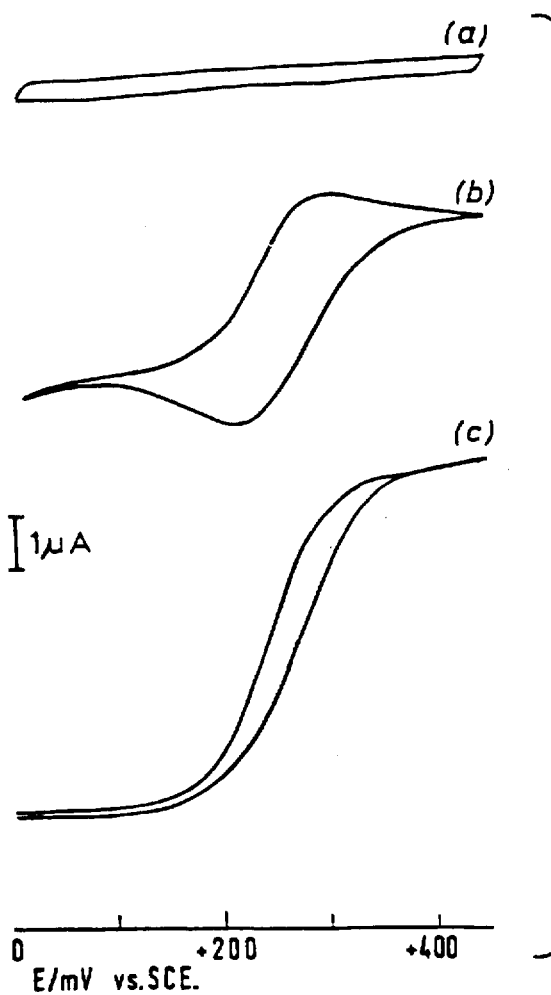
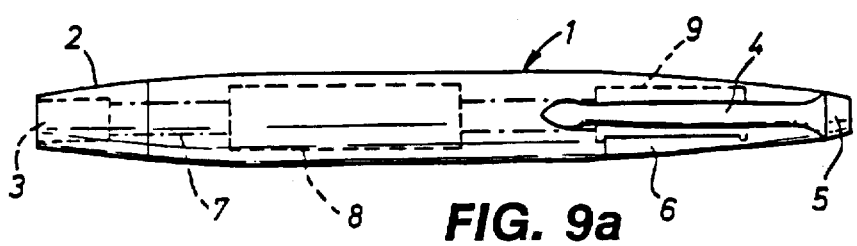
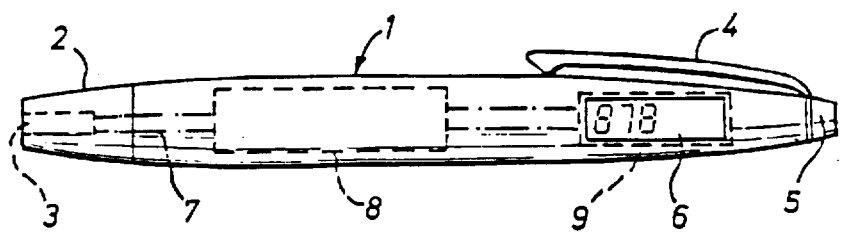
FIG. 8
FIG. 9a
FIG. 9b 5,727,548

1

STRIP ELECTRODE WITH SCREEN PRINTING

CROSS-REFERENCE TO RELATED APPLICATIONS

This is a continuation of application Ser. No. 08/281,237 filed Jul. 27, 1994; now U.S. Pat. No. 5,509,410 which is a continuation of Ser. No. 07/905,504, filed Jun. 25, 1992, now abandoned; which is a continuation of U.S. Pat. No. 07/762,657, filed Sep. 19, 1991; which is a continuation of U.S. Pat. No. 07,762,657, filed Sep. 19, 1991; which is a continuation of U.S. Pat. No. 07/429,055, filed Oct. 30, 1989; which is a divisional of U.S. Pat. No. 07/002,120, filed Jan. 12, 1987; which is a continuation-in-part of U.S. Pat. No. 06/607,599, filed May 7, 1984, now abandoned; which is a continuation-in-part of U.S. Pat. No. 06/590,864, filed Mar. 19, 1984. The following U.S. patent applications filed May 7, 1984 and owned by applicants' assignee, Halisense, Inc. are hereby incorporated by reference: Sensor For Components of A Liquid Mixture (U.S. Ser. No. 607,699); Assay Techniques Utilizing Specific Binding Agents (U.S. Ser. No. 607,695); Assay Systems Using More Than One Enzyme (U.S. Ser. No. 607,698); Assay Systems Utilizing More Than One Enzyme; (U.S. Ser. No. 607,607).

BACKGROUND OF THE INVENTION

This invention relates to enzymatic sensor electrodes and their combination with reference electrodes to detect a compound in a liquid mixture.

Various electrochemical sensors are known which employ enzymes to sense the presence of a compound that serves as an enzyme substrate. As just one example, Nakamura U.S. Pat. No. 4,224,125 discloses an enzyme electrode system in which an enzyme, such as glucose oxidase, is used to sense glucose. A redox compound is used to accept electrons from the enzyme. For example, at 10:21–49, Nakamura discloses (FIG. 5) press molding to the electrode a mixture of glucose oxidase cross-linked by gluteraldehyde and a fluorocarbon polymer powder together with a cation exchange resin containing potassium ferricyanide. Nakamura's electrode system (FIG. 2) consists of three electrodes: an enzyme electrode 7, a reference electrode 8, and a counter electrode 10.

In another example, Pace U.S. Pat. No. 4,225,410 discloses a multi-layer enzyme sensor; for example sensor 14b (FIG. 7b) measures levels of lactate dehydrogenase. NAD$^+$ is generated at a fourth electrode 82, and the enzymatic reaction converts it to NADH which is sensed at monitoring electrode 84 by undisclosed means. A barrier/counter electrode 80 and a reference electrode 85 are used in conjunction with monitoring electrode 84.

SUMMARY OF THE INVENTION

One aspect of the invention generally features a two-electrode strip for releasable attachment to signal readout circuitry, forming a sensor system that detects a current representative of a compound in a liquid mixture. The strip comprises an elongated support (preferably flat) adapted for releasable attachment to the readout circuitry; a first conductor and a second conductor each extend along the support and comprise means for connection to the circuitry. An active electrode, positioned to contact the liquid mixture and the first conductor, comprises a deposit of an enzyme capable of catalyzing a reaction involving the compound. Electrons are transferred between the enzyme-catalyzed reaction and the first conductor to create the current. A reference electrode is positioned to contact the mixture and the second conductor.

The preferred embodiment of the strip includes the following features. An electron mediator (most preferably a ferrocene) is included in the active electrode deposit to effect the electron transfer. The compound being detected is glucose, and the enzyme is glucose oxidase or glucose dehydrogenase. The active electrode and the reference electrode are coatings applied to the elongated support, e.g. the active electrode is formed by printing (e.g. screen printing) an ink comprising a conductive compound, the enzyme and the mediator, and the reference electrode is also formed by screen printing. The means for connecting to the readout circuit are positioned toward one end of the elongated support, and the electrodes are positioned remote from that end.

In a second aspect, the invention features apparatus that includes the above-described strip and circuitry adapted to provide an electrical signal representative of the current. The read-out circuitry comprises an amplifier to amplify the current, a low-pass filter connected to the amplifier output, a current-to-voltage converter connected to the filter output, and a means to display a value representative of the output of the converter. The apparatus also includes means to maintain a substantially constant bias voltage across the electrodes during current measurement, even without a separate voltage reference in contact with the mixture.

In a third aspect, the invention features screen printing the enzyme onto a substrate to form an enzymatic sensing electrode. The ink used for screen printing includes a liquid vehicle, a suspension of conductive material, and the enzyme. Preferably, it also includes a mediator capable of transferring electrons between the enzymatic reaction and a conductor on the substrate. Also preferably, the substrate is a flexible, high-dielectric polymeric substance, such as polyvinyl choride, polyester, or polycarbonate.

The invention enables a very small, inexpensively manufactured, disposable electrode strip that provides an accurate electronic readout of the target compound. In particular, the active electrode is sized to be covered by the smear of blood produced from a drop of blood (even a non-expressed drop) generated from a needle-prick at a bodily extremity, and the reference electrode is sized and spaced from the active electrode a distance such that the reference electrode is covered by the same smear of blood.

Other features and advantages of the invention will be apparent from the following description of the preferred embodiment.

DESCRIPTION OF THE PREFERRED EMBODIMENT

We first briefly describe the drawings.

Drawings FIG. 1 is a front view of a strip-supported electrode configuration;

FIG. 2 is a back view of the combination shown in FIG. 1;

FIG. 3 shows an alternative strip-supported electrode;

FIG. 4 shows a strip-supported electrode which is a variant of FIG. 3;

FIG. 5 shows a modified connection of the strip electrode of FIGS. 3 and 4;

FIG. 8 shows diagrammatically the electrical performance of electrodes as described in the above Figures, with especial reference to FIGS. 6 and 7;

FIGS. 9I and 9b are general diagrammatic side views of a pen-like portable holder, of particular utility for the electrodes shown in FIGS. 3, 4 and 5, having an assembly of circuitry and having a read-out window;

Electrode Structure

Figure 6:
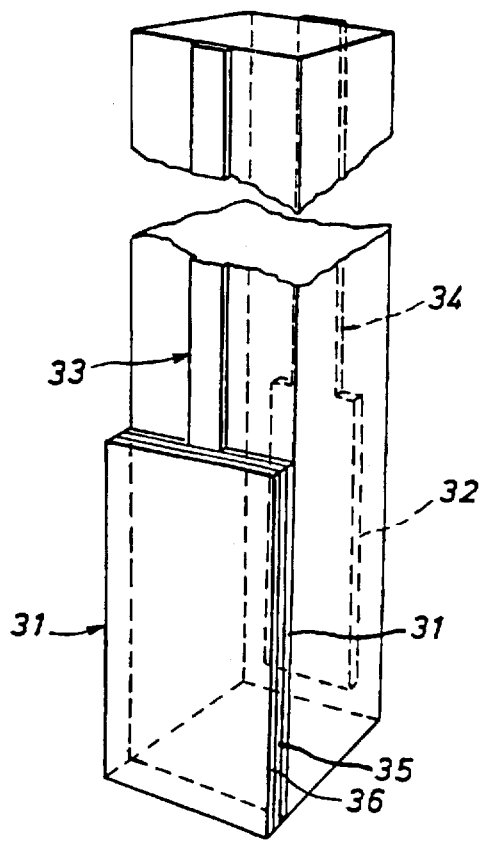
FIG. 6 shows a further alternative supported electrode.

In general, the strip electrode of the invention comprises a conductive electrode coated with a mixture, or layers, of a catalytically active enzyme and a mediator compound and usually further coated with a retaining permeable membrane. When such a coated electrode is contacted with a substrate containing a species for which the enzyme exerts a catalytic effect, the mediator compound transfers charge to the electrode and this can be used to give a readout signal, against a standard electrode, correlated with the concentration of the said species, even in the presence of other species since enzymes are typically highly selective in their catalytic action. Commonly owned Ser. No. 607,699 generally describes methods of coating a conductive electrode with enzyme and mediator; that application is hereby incorporated by reference. The mediator compounds described in Ser. No. 607,699 include polyviologens, fluoranil and chloranil. However, the preferred mediator compounds are metallocene compounds, and in particular the ferrocenes (biscyclopentadienyl iron and its derivatives).

The particular advantages of ferrocenes are as follows: (a) a wide range of redox potentials accessible through substitution of the cylopentadienyl rings (b) functionalization of the rings, e.g., to confer solubility or chemical linkability to other such rings or other system components (c) electrochemically reversible one-electron redox properties (d) pH-independent redox potential and (e) slow autooxidation of the reduced form.

The ferrocene structure may be modified by substitution on the rings, and/or by association or polymerization, which modifications affect the physical, chemical and electrical behavior so that optimization of a particular sensor electrode material is possible. In general use, the compound 1,1'-dimethylferrocene is a valuable mediator. The particular enzyme employed may be selected from a range of enzymes including the following:

| Enzyme | Substrate |
|---|---|
| Flavo-Proteins | |
| Pyruvate Oxidase | pyruvate |
| L-Amino Acid oxidase | L-Amino Acids |
| Aldehyde Oxidase | Aldehydes |
| Xanthine Oxidase | Xanthines |
| Glucose Oxidase | Glucose |
| Glycollate Oxidase | Glycollate |
| Sarcosine Oxidase | Sarcosine |
| Lactate Oxidase | Lactate |
| Glutathione Reductase | NAD(P)H |
| Lipoamide Dehydrogenase | NADH |

-continued

| Enzyme | Substrate |
|---|---|
| PQQ Enzymes | |
| Glucose Dehydrogenase | Glucose |
| Methanol Dehydrogenase | Methanol and Other Alkanols |
| Methylamine Dehydrogenase | Methylamine |
| Haem-Containing Enzymes | |
| Lactate Dehydrogenase (Yeast Cytochrome b2) | Lactate |
| Horse-Radish Peroxidase | Hydrogen Peroxide |
| Yeast Cytochrome c Peroxidase | Hydrogen Peroxide |
| Metalloflavoproteins | |
| Carbon Monoxide Oxidoreductase | Carbon Monoxide |
| Cuproproteins | |
| Galactose Oxidase | Galactose |

The strip electrode has the following design criteria. The electrodes on the strip should be as small as possible and the strip should preferably be disposable. The strip should be elongate for ready handling as an electrode for ready assembly to equipment on the one hand and contact with the sample on the other. It must be sensitively manipulable. It must carry, prior to assembly or in the assembled structure, the reference electrode as well as the 'sensitive' electrode, in spaced non-contiguous relationship.

The invention is particularly useful for selective detection, measurement or monitoring of a given dissolved substrate in a mixture of dissolved substrates.

The elongate support could be a rod or tube, but conveniently it comprises a flat strip.

The active electrode is preferably formed of carbon e.g., a filter paper containing carbon. We have also found that carbon foil e.g., as available under the Trade Marks "GRAPHOIL" or "PAPYEX" is a valuable electrode material. The enzyme thereon can in theory be any enzyme, e.g., those listed in U.S. Ser. No. 607,699, and itemized above but the use of glucose oxidase or dehydrogenase, e.g., the bacterial glucose dehydrogenase from *Acinetobacter calcoaceticus* is particularly valuable. Any suitable mediator compound can be used, but ferrocene or ferrocene derivatives (expecially 1,1'-dimethylferrocene) are greatly to be preferred.

By way of example only, carbon foil can be glued to the strip; 1,1'-dimethylferrocene mediator can be deposited on the surface of the foil by evaporation of a toluene solution; and enzyme can be bonded to the surface by the use of 1-cyclohexyl-3-(2-morpholinoethyl) carbodiimide metho-p-toluene sulphonate (referred to below as "carbodiimide").

The reference electrode can be any convenient reference electrode. We have found it useful to provide adjacent but not contiguous to the first electrode, a flat layer of silver and to convert the surface thereof to silver chloride so as to give an Ag/AgCl reference electrode.

Typically, the electrical connections can be wires which extend down, and are preferably adhered to, the strip, and make electrical contact each with its respective electrode.

The readout means is preferably a digital indicator suitably connected to a dedicated potentiostat which poises the carbon electrode potential at e.g. +150 mV vs. Ag/AgCl for a glucose system. The current flowing is then proportional to glucose concentration.

In a particular valuable version of this type of sensor, it comprises (a) a flat first electrode area of known area small enough to be completely coverable by the smear of blood produced from a non-expressed drop of blood generated from a needle-prick at a bodily extremity, (b) a reference electrode area on the same surface separate from but sufficiently close to the sensitive electrode area that the said blood smear also reaches the reference electrode to establish electrical communication, and (c) conductive elements extending separately along the same surface of, and thus insulated from the elongate support member, communicating one with each electrode for connection to signal readout means attachable to one end of the member.

The area of the first (i.e. sensitive or active) electrode is generally substantially square; it may be rectangular or otherwise shaped, but in any case usually will correspond in area to a square of 5 mm edge length, or below e.g., from 2 to 4 mm.

For convenience, this document will refer hereinafter to blood-glucose-measuring equipment as being typical but not limitative of equipment with which the present invention is concerned.

Diabetic subjects need to measure their glucose levels frequently. Hitherto, a common method carried out by the subject personally is colorimetric test using a blood or urine sample which is applied over a surface area containing a color-reactive detector chemical, adjacent to a comparison area, to give a color change which is compared with a chart of color values as an approximate measure of glucose level.

There are however, defects in this method. Firstly, colorimetric changes are quantitatively difficult to assess, especially if the patient has impaired vision as a result of the diabetic condition. Indeed, because of this problem expensive automatic color comparison equipment may need to be purchased by some subjects for interpreting the test results. Secondly, the blood test, while inherently more accurate than a urine test, needs a large enough sample to cover the test surface. Thirdly, it requires the patient to time the color development accurately. Since blood samples, on a self-treatment basis, are taken from body extremities (fingers, toes, earlobes), they are normally not large enough when obtained by a simple needle-prick, and must in fact be expressed i.e., squeezed or massaged out to form a larger drop. Progressively, the tissue of the extremities becomes scarred and coarsened by such treatment to an extent whereby finding fresh testing sites presents a problem.

In order to embody the invention on a home-diagnostic basis, a main object of the present invention in one aspect is as described above the provision of small scale non-traumatic test pieces as an external test electrode strip capable of using the naturally-arising small blood droplet from a needle-prick tester, without tissue massage. Examples are described in more detail below.

These small-scale electrodes are intended as single-use throwaway articles and are utilized in conjunction with electrical circuitry and a readout means, to which they must be easily attachable and detachable. Such circuitry and readout means is itself preferably embodied on a very small scale.

We have accordingly found that the totality of the equipment is subject to certain design constraints.

Thus, it is further object of the invention in this form that the device should be nontraumatic to the user either physically e.g., if used with its own invasive probe or psychologically by virtue of its appearance.

It is further object of the invention in this form that the device should be capable, despite the small size of the throwaway electrode and of the permanent circuitry/readout components, or easy assembly and disassembly even by juvenile or elderly lay users.

It is still a further object of the invention in this form to ensure the relatively expensive permanent circuitry/readout components should, despite their small size, be of a form which minimizes loss or damage.

It is still a further object of the invention in this form to provide a device the display readings of which are visible and understandable to a non-expert user.

We have now found that these and other objects of the invention can be met by assembly the circuitry/readout components into a housing resembling a pen/digital-watch.

According therefore another aspect of the present invention there is provided an assembly of circuitry and display means for use in producing a readout value as a diagnostic aid in human or veterinary medicine, housed in a pen-like hollow elongate housing having (a) at one end an electrically conductive socket suitable to receive the outer end of at least one detachable test member capable of producing an electrical signal correlating with a physiological parameter to which the test member is selectively sensitive and (b) towards the other end a digital readout window for exhibiting a numerical value corresponding to the parameter. A thermistor may also be used for temperature compensation.

The person skilled in the art of designing medical equipment will appreciate that the invention extends not only to the pen-like assembly as defined above but also to the combination of such an assembly with an attached test member, and to the combination as a kit of interrelated parts of such an assembly with a plurality of test members suitable for one-off use.

The term "pen-like" is a general limitation on size and shape. In functional terms, its characteristics are such that it can be held near the socket between the thumb and the nearer one or two opposed fingers, with the elongate body resting on and extending beyond the forefinger, but not to an extent that prejudices fine control of the socket end by the thumb and fingers. In numerical terms it can be from 10 to 30 cm. long and from 0.5 to 3 cms across its maximum transverse dimension; more usually it will be from 12 to 20 cms. long and from 0.8 to 1.5 cms. across. It can be generally circular, or polygonal, in cross-section. Each detachable test member is usually a small-scale enzyme-coated sensor electrode, of the type discussed in U.S. Ser. No. 607,699, and especially such an electrode where the enzyme is specifically glucose-catalyzing whereby diabetic conditions can be measured. It may alternatively be a flat external strip electrode dimensioned to operate on a small, non-expressed, blood droplet. The socket arrangement will vary accordingly.

In one embodiment of the present invention, two or more sensor electrodes may be incorporated into a single test member. Again, the socket arrangement will vary accordingly.

The readout means will typically be a conventional seven-segment display window towards the rearward end of the "pen" as in conventional pen/watches. In the case of the multiple sensor embodiment described in the preceding paragraph the display may be switchable between each sensor's discrete monitoring circuit, both the display and a single monitoring circuit may be switchable between sensors, or a specific display may be provided for each of the sensors present.

I. Constructional features

(a) Membrane cover for electrode

Although the enzyme electrode should be in electrical contact with the liquid, it may be found valuable to exclude the sensor from interfering contact with larger molecules or tissue fluid components. This can be done by a covering or surrounding membrane, depending on electrode geometry. Heat-shrinkable thin polymer tubing can be used as, or in connection with, such membranes.

The membranes can be polymerized in situ. A particular valuable membrane is formed by polycarbonate, especially those polycarbonates sold under the Trade Marks "NUCLEOPORE" or "STERILIN". When tissue fluids are examined they may contain ascorbate; polycarbonate membranes do not permit the passage of ascorbate and thus virtually eliminate interference from that substance. Alternatively, a polyurethane membrane may be employed.

(b) Type of carbon

Carbon foil, as strips, or carbon attached to metal meshes, of pyrolytic grade and known by the Trade Marks "GRAPHOIL" and "PAPYEX" are much preferred for carbon-ferrocene electrodes for use with glucose oxidase. Oxygen interference is minimal, there being less than 4% change in signal between anaerobic and fully aerobic samples. Their physical nature is also very convenient for fabrication, especially of small-scale devices.

II. Operational features

(a) Operational potential

Preferably operation should take place at a potential equivalent to +50 to +200 mV vs. SCE since intereference caused by oxidation of other chemical species present is thereby reduced.

(b) Concentration range

Glucose oxidase can be used to monitor glucose concentrations of 0 to 40 mM, and glucose dehydrogenase at 0 to 20 mM when immobilised on a carbon-ferrocene electrode. The sensor response is linear up to about 40 mM.

(c) Response times

The glucose oxidase sensor without membrane is kinetically limited giving rapid response times i.e., about 20 seconds to 95% of the steady-state current response.

(d) Oxygen-sensitivity

Glucose dehydrogenase/ferrocene electrodes are totally oxygen-insensitive.

(e) Use of third electrode

In practice, a realistic device can achieve good performance without a third electrode, using Ag/AgCl as a reference counterelectrode, as described more fully below.

(f) pH and temperature

Glucose oxidase electrodes show no change in current output between pH6 and pH9, and are thus relatively pH-insensitive. They are temperature-stable up to 40° C. If necessary temperature compensation can be effected using a thermistor, or a constant temperature jacket may be used. Also, operating with the electrodes diffusion-limited minimises temperature effects.

(g) Storage of electrodes

Electrodes may be stored moist. Extended storage, over months or years, may be achieved by freeze-drying or air-drying.

Although the invention as defined above has been discussed in terms of the equipment used, it will be appreciated that other aspects of the invention also present themselves. The totality of the equipment may include a replaceable or throwaway cell; thus, the cell per se as defined above is an aspect of the invention, as are the combination of electrodes irrespective of details of cell design, and the individual electrodes, of novel configuration. Methods of detecting the presence of, measuring the amount of or monitoring the level of one or more desired components (e.g., glucose) of a liquid mixture (e.g., tissue fluid or liquids derived therefrom) utilizing the equipment cells or electrodes cells defined above are also a feature of the present invention.

Finally, the present invention is concerned with the electrical circuitry for operating the equipment as described.

According to this aspect of the present invention there is provided a measuring device for use with an electron-transfer electrode, comprising means for comparing an electrical output of the electrode with an electronic reference and means for providing a signal related to the electrical output of the electrode.

By employing an electronic reference rather than a cell of reference electrode a measurement using a sensor including an electron-transfer electrode may be made without the use of a separate electrode as a reference.

In a preferred embodiment of the invention, the electron-transfer electrode is poised at a fixed potential against a reference electrode, and the current flowing in the electron-transfer electrode is measured.

In the following description of FIGS. 1 and 2 dimensions, materials, amount and proportions are given by way of example only.

In FIGS. 1 and 2, a strip of epoxy glass 1, 9.5×40×1.6 mm, has two 1 mm diameter holes 2 and 3 therein. A 9×9 mm piece of graphite tape of foil 4 is glued on one face, near the end to cover hole 2 and a 4×9 mm strip of silver foil 5 is glued adjacent thereto over hole 3. Wires 6 and 7 (FIG. 2) on the back enter holes 2 and 3 respectively for electrical connection with the respective electrode material 4 and 5, being glued in the holes by conductive epoxy resin 8. A stabilizing layer of epoxy resin is present over at least part of the back e.g., at 9 to keep the wires in place. Carbon electrode 4 is covered with 1, 1'-dimethylferrocene and glucose oxidase. Silver electrode 5 is covered with silver chloride.

The strip is made up in the following sequence:

(a) drill holes 2 and 3, (b) glue on electrodes 4 and 5; "ARALDITE" epoxy resin is suitable but should not enter holes 2 and 3, (c) attach wires 6 and 7, using conductive epoxy 8, and apply "ARALDITE" resin at 9 to fix the wires in place, (d) hold the silver electrode at +40 mV vs. SCE in 5M for 10–15 seconds to deposit a thin AgCl layer, (e) apply a solution of 1,1'-dimethylferrocene (4:1) in toluene (20 mg/m) to the graphite tape 4 and allow to evaporate, (f) cover the ferrocene-coated tape with 50 µl of carbodiimide (25 mg/ml) in pH 4.5 acetate buffer for 1½ hours and (g) rinse and cover with glucose oxidase (12.5 mg/ml) in pH 5.5 acetate buffer for 2 hours.

The strip can be used by attaching wires 6 and 7 to a potentiostat poising the potential at electrode 4 at +150 mV. vs. Ag/AgCl, and dipping the strip into a glucose-containing solution so that both electrodes 4 and 5 are covered. The shape of the strip facilitates such handling. The current flowing is proportional to glucose concentration.

FIG. 3 shows a strip electrode 17 made of, for example, a ceramic material or printed-circuit-board laminate. It includes a square area 18 with connector lead 19, the square being covered with the enzyme-containing layers as described above. It further includes a small reference electrode area 20 and separate connector lead 21. The rearward end 22 of the electrode 17 fits into a socket as shown in FIGS. 13a and 13b and described below. It is to be noted that, as with the needle 10, the electrode stip 17 is a small-scale device. Thus, square area 18 is of a side length only about half that of each of two square colourimetric test areas of conventional diagnostic tests and can be used with the original non-expressed bead of blood from a needle-prick device, which is adequate to cover the whole of the square area and communicates electrically with reference electrode area 20.

Modifications may be made to the embodiments shown in FIG. 3. For example, the strip electrode as shown in FIG. 3 can be longer, whereby electrodes 18 and 20 are located only partway along the strip, leaving a free end 22a to facilitate ease of handling by the patient without damaging or touching the electrodes. Also, the electrode strip can clip within two opposed contacts of resilient mounting 29, the routing of one or other of conductive lines 19 and 21 being modified accordingly.

FIG. 4 shows a longer strip and FIG. 5 shows the inner end of the strip held between two resilient metal contact strips.

In FIG. 6 a 2 cm length of electrically insulating polymer for example MYLAR or TEFLON (a polyfluorocarbon) 0.3 mm square in transverse cross-section is provided with a palladium-silver conductive electrode 31, on the front surface as shown, and a second, smaller electrode 32, on the back as shown in dotted lines. In each case conductive lines 33 and 34 respectively, were formed simultaneously with the electrodes.

On the front electrode 31 is painted a mixture of toluene, 1,1'-dimethyl ferrocene and graphite, formed by mixing a solution of the toluene and 1,1'-dimethyl-ferrocene and a slurry of toluene and graphite. It is believed that the ferrocene is adsorbed onto graphite particles. After drying the mixture forms a layer 35. A layer 36 of glucose oxidase is then immobilized on the graphite surface by carbodiimide immobilisation, known per se (enzyme adsorption can also be used). The electrode may then be covered, on both sides, with a semipermeable membrane of cellulose acetate (or polyurethane), not shown, to block large interfering species from contact with the electrode.

The square section of the support helps in the painting of slurry, or the enzyme-attachment stage's, in keeping the electrodes 31 and 31 distinct.

Figure 7:
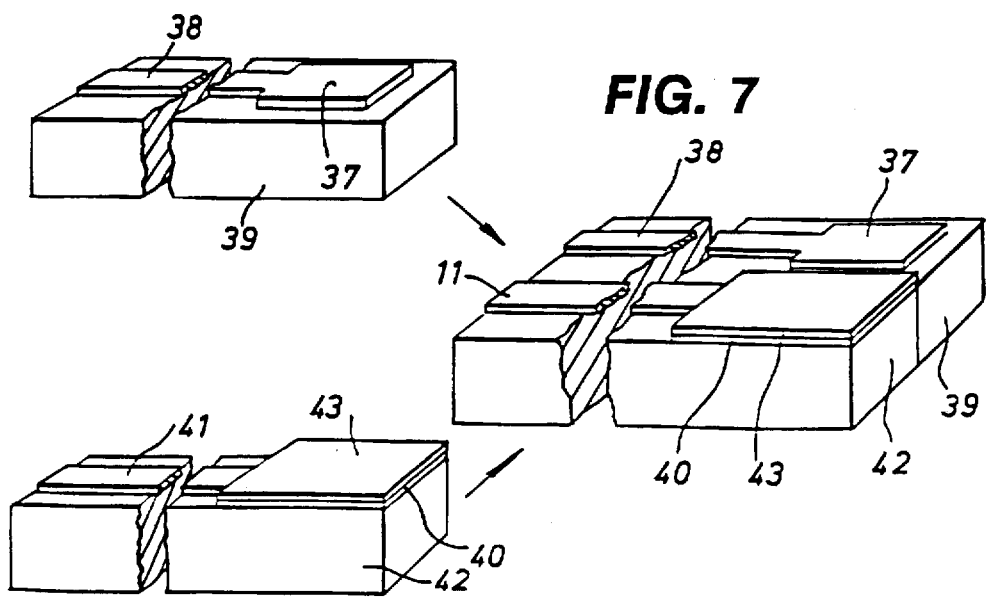
FIG. 7 shows a combination of two electrode supports.

FIG. 7 shows the key steps of a procedure which can be used to advantage in the fabrication of these microelectrodes.

The reference electrode 37 and its conductive lead-out strips 38 are formed in silver/palladium on TEFLON base 39. Similarly, an electrode support 40 and lead-out strip 41 are formed in silver/palladium on TEFLON base 42. Only this base 42 and its electrode support are then subjected to (a) painting on a graphite slurry in toluene (b) dipping in 1,1'-dimethylferrocene solution in toluene and (c) contacting with the enzyme to absorb e.g., glucose oxidase into the active layer 43. Thereafter the bases 39 and 42 are glued or held, side-by-side, their general rectangular cross-section facilitating such positive location. Back-to-back location is also possible.

As before, the finished assembly may be located inside a needle bore, e.g., with extra access portions near the electrode surfaces.

FIG. 8 shows results obtained when the 0.3 sq. mm prototype electrode of FIG. 6 was characterised electrochemically and is generally indicative of results obtained with other electrode designs.

First, a solution of graphite powder plus a binder in toluene was painted on the palladium-silver alloy conductor 31 (supplied by Ferranti) and allowed to dry. Curve (a) shows a direct current cyclic voltammogram of the electrode in 100 mM phosphate-perchlorate buffer at pH 7.0. The potential was scanned over the range 0 to +500 mV vs. SCE. The electrode surface was mechanically sound and could be polished with an alumina-water slurry without affecting its response.

Reference electrode

The reference potential of the palladium-silver reference electrode 32 (incorporated onto the strip) was determined by substitution into an electrochemical system which had previously been calibrated with a saturated calomel electrode (SCE). The reference potential was 60 mV negative of SCE, consequently the glucose sensor should be operated at 160 +200 mV vs. Ag/Pd. The reference potential was stable, i.e. did not drift, over 48 hours of operation.

Electrochemical response of graphite electrode

Curve (b) shows a direct current voltammogram of ferrocene monocarboxylic acid recorded at the graphite electrode.

Curve (c) shows that a catalytic current flows upon the addition of glucose and glucose oxidase to the solution described in (b). Together, these curves demonstrate that the electrode formed the basis of a glucose sensing device.

Incorporation of 1,1'dimethylferrocene into the electrode

A solution of 1,1'dimethylferrocene in toluene was mixed into a toluene-based slurry of the graphite powder. The mixture was then painted on to the base conductor 31 and allowed to dry at 35° C. This provided an electrode surface that was electroactive towards glucose oxidase.

Conclusions

These experiments showed that "thick layer" or screen-printing technology could provide a usable base strip which could easily be coated with a stable graphite surface and that moreover the electrode surface could be made electro-active towards glucose by adsorption of a ferrocene directly into the coating mixture. In addition, the reference electrode operated satisfactorily in buffered solutions.

FIGS. 9a and 9b show a holder which is particularly adapted to utilize electrodes as shown in FIGS. 3, 4, 5 but which could if necessary utilize electrodes as shown in FIGS. 1 and 2, 6 and 7 at least of the various embodiments shown.

From above the holder 1 intentionally resembles a conventional pen/watch as much as possible. It has a forward end 2, possibly rotary to tighten the walls of a flattened socket cavity 3 formed within it. A central joint, a clip 84 and a press-button 5 all resemble those of a conventional pen, and digital readout-window 6 is also of a type known in pen/watches.

Inside the holder as shown by dotted lines is connection circuitry 7, possibly printed in situ, battery 8 and operating circuitry 9 behind and manufactured as a unit with the display window 6. The display can be capable of operation only when button 5 is pressed so that extra illumination can be provided if necessary.

The embodiments shown in FIGS. 9a and 9b especially when used in conjunction with the electrodes of FIGS. 4–6 fulfill the design criteria discussed above for such portable equipment.

The delicate manipulation facilitated by the pengrip (e.g., by thumb and finger) means that the small electrodes e.g., of FIGS. 3, 4, or 5 can be easily assembled into, or detached from, the socket. A user will always orient the holder with the window 6 visible thus, always giving a uniform relative orientation to the socket 3 whereby the rearward ends of the fragile electrodes can be fitted without experiment and damage.

The "pen format is instinctively picked up after use and safely carried in a pocket, more so than for any other small device. Thus, the expensive part of the equipment is safeguarded. Furthermore, it is possible to incorporate a conventional timer circuit into the device thereby fulfilling the actual function of a pen-type watch and providing an audible or visible signal which marks the point in time at which a reading should be taken.

Finally, the display is numerical, clearly visible and if necessary can be supplemented by an illuminating light source.

Figure 10:
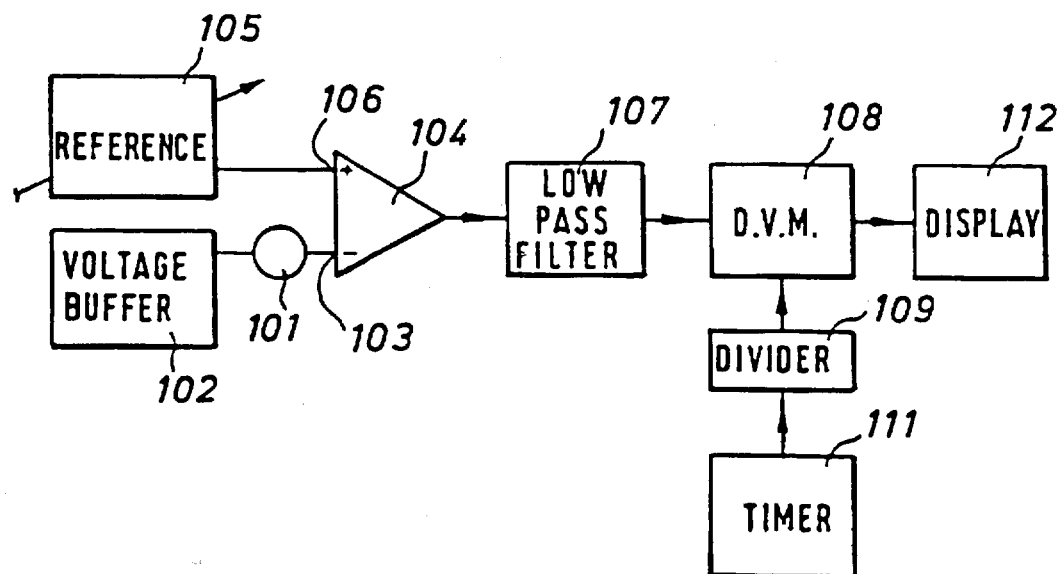
FIG. 10 shows a schematic diagram of one form of electrical circuitry for use with the electrodes and equipment of the present invention.

In FIG. 10, a sensor 101 is connected between a voltage buffer 102, and the inverting input 103 of the operational amplifier 104 which is configured as a current amplifier. An electronic reference 105 connected to the non-inverting input 106 of the operational amplifier is fed into a low-pass filter 107 which removes rapid signal fluctuations (which may be due to noise, earth hum or other sources of interference) while allowing the filtered output of the operational amplifier 104 to be fed into the digital voltmeter (D.V.M.).

The digital voltmeter is supplied with clock pulses via the divider 109, from the timer 111. The D.V.M. drives a liquid crystal display 112. The electronic reference 105, is either of a pre-selected value or capable of being selected for a particular electron transfer electrode.

In each of the embodiments of electrode discussed above the sensor comprises a mediator-carrying surface which has one or more enzymes immobilized thereupon. The sensor further includes a silver/silver chloride (Ag/AgCl) internal reference electrode. If, for example, a voltage of +200 mV volts is preferentially dropped across the electrode as is the case with a glucose-oxidase-containing electrode, then the reference voltage 105 is selected accordingly.

Figure 11:
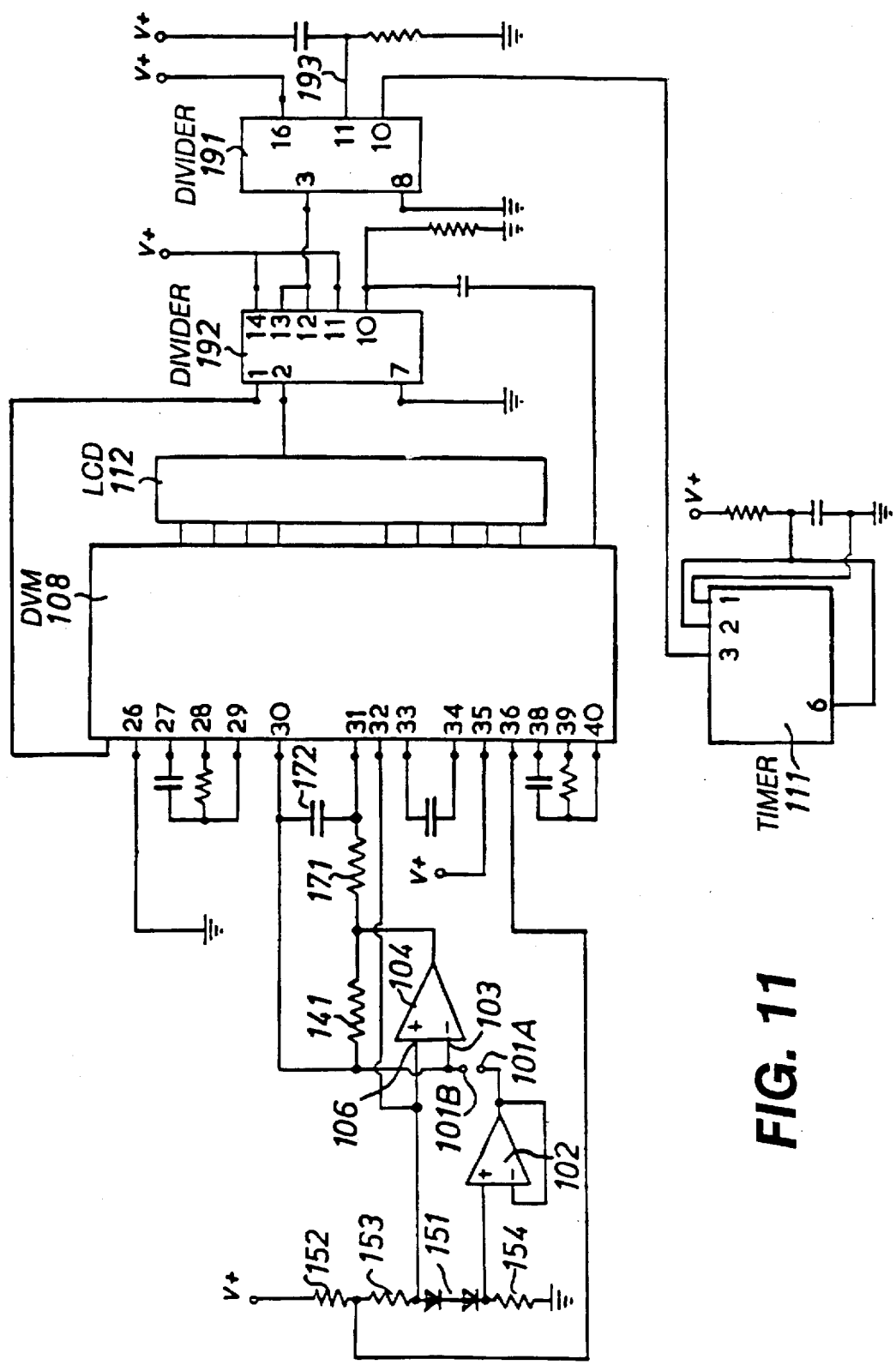
FIG. 11 shows a more elaborated circuit diagram for use in the embodiment of FIG. 10.

In FIG. 11, the electronic reference comprises resistors 152, 153 and 154 together with diodes 151. A voltage is selected at 0.3 V by a suitable choice of resistor values at 152, 153 and 154. The voltage across the resistor 153 is 1 V, which ensures that 100 µA of electrode current will give a full scale reading of 999 on the liquid crystal display 112.

Non-inverting buffer 102, ensures that the voltage on the terminal 101A remains substantially constant. The sensor 1 (FIG. 1) is connected across terminals 101A and 101B.

The operational amplifier 104 is connected via its inverting input 103 to the terminal 101B and the feedback resistor 141. The non-inverting input 106 is connected to the electronic reference.

A first-order low-pass filter 171, 172 is connected across the feed-back resistor 141, and supplies an analog signal to the D.V.M. 108. Pin values are given for a 7116CPL chip (manufactured by Motorola). The D.V.M. drives a liquid crystal display 112.

Clock pulses for the D.V.M. are supplied from the timer 111, (pin values are given for a 555 chip) via the dividers 191 (pin values for an MC 14020B) and 192 (pin values for an MC140106B chip). The connection 193 to pin 11 of the divider 191 enables a power-up reset.

Figure 12:
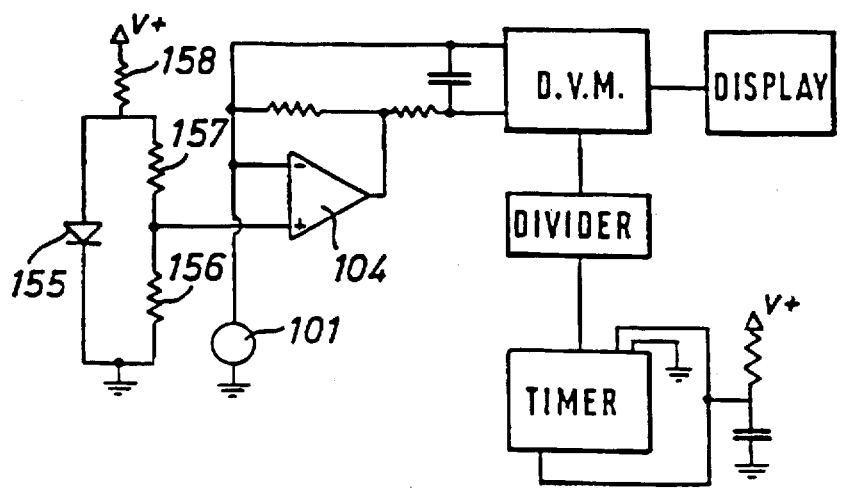
FIG. 12 shows a schematic diagram of an alternative embodiment of electrical circuitry.

In FIG. 12, an alternative circuit is shown which does not make use of the non-inverting voltage buffer 102, but has the sensor 101 connected between the operational amplifier 104, and ground. The embodiment shown in FIG. 12 employs a fixed reference voltage which is provided by a circuit differing from that of FIG. 11.

In this embodiment, the diode 155 functions as a voltage-reference diode and provides a reference voltage drop across its ends equal to the diode forward voltage.

By a suitable choice of the values of the resistors 156, 157 and 158 the correct voltage may be applied across the electrode. In this embodiment the sensor again employs as a reference an Ag/AgCl couple and immobilized glucose oxidase in the presence of a mediator compound as the electron-transfer electrode.

Figure 13:
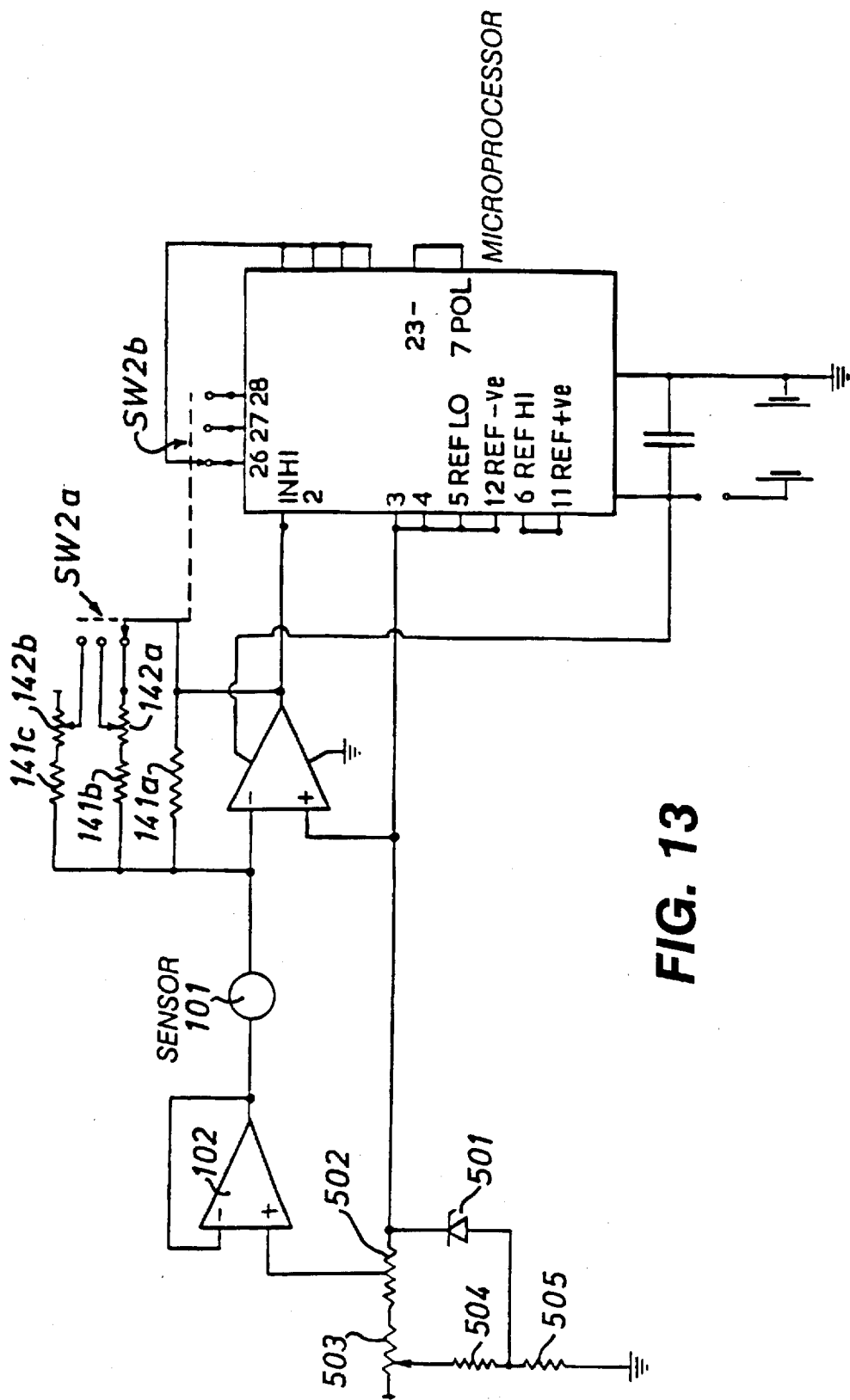
FIG. 13 shows the more elaborated circuit diagram of a yet further embodiment of circuitry.

FIG. 13 shows a third embodiment of the present invention, which provides a continuously variable reference voltage which may be selected to accommodate any type of electron-transfer electrode, that is, one, which for example, employs any of the enzymes listed herein or any combination of these enzymes. The LCD display is not shown in FIG. 13.

In FIG. 13 the feedback resistor 14 in circuit at any given time may be selected from resistors 141a, 141b, and 141c by means of switch SW2a which is gauged with switch SW2b. This allows the current output of the sensor 101 to be displayed in three ranges, for example, 1 µA, 10 µA or 100 µA full scale.

The embodiment shown in FIG. 13 has the non-inverting voltage buffer 102 of the embodiment shown in FIG. 11.

The reference voltage for the embodiment shown in FIG. 13, is derived from the circuit elements 501–505 which include the potentiometers 503 and 502 providing a variable voltage across the sensor 101, thereby accommodating any type of electron-transfer electrode. It is envisaged that the continuously variable resistors 142a and 142b could by replaced in certain applications by stepwise resistance switching means with each position or setting being dedicated to a particular type of electrode.

Various modifications may be made in the circuitry. For example the liquid crystal display may be replaced by a plotter or a dosage control device, or a temperature stability circuit may be incorporated.

Various modifications may also be made in constructional techniques e.g., in a multi-stepped procedure comprising:

I - screen printing of Ag/AgCl reference electrode and metal tracing.

II - screen printing of the active electrode with a printing ink comprising a colloidal carbon, glucose oxidase in buffer, and an organic polymer.

III - screen printing, spraying or dip coating to provide a membrane over the assembly.

Advantages of this method are that it is amenable to high volume automation, and is of high reproducibility.

From the above it follows that a suspension in a liquid medium of carbon together with at least one of (a) an enzyme and (b) a mediator compound capable of transferring charge to the said carbon from the enzyme when the enzyme is catalytically active, the said suspension being formed as a printable and conductive ink for use in the fabrication of electrodes as described above, it also an aspect of the invention. Preferably, both the enzyme (e.g., glucose oxidase) and the mediator (e.g., ferrocene or a ferrocene derivative) are present in the ink formulation and form a single layer admixture such as layer 43 of FIG. 7, laid down by screen printing rather than being applied in three steps as previously described.

The mediator may be in the form of a mediator/hapten conjugate, i.e., be linked to a ligand material so that its activity in its charge-transferring property is a measure of further or competitive binding reaction with a specific binding agent with which the eventual electrode, having the specialized ink thereon, is contacted. A specific example is the theophylline/ferrocene conjugate described in copending application U.S. Ser. No. 607,698, filed May 7, 1984 entitled "Assay systems utilising specific binding agents". Other mediato/enzyme/ligand systems can also be utilised in the specialised ink.

Other Embodiments

While not claimed in this application, it should be apparent that the strip electrode can take the form of other embodiments, and can be used with other inventions. For example, it could be used with the invention of copending application Ser. No. 607,695 entitled "Assay technique utilising specific binding agents", featuring the effect on the enzyme and/or mediator's electrochemical availability of specific binding agents e.g., antigens/antibodies and others. For example, the area of first electrode material may comprise (a) a ligand such as an antibody (b) an antiligand, such as a hapten, with specific binding properties thereto (c) the mediator, conjugated to either (a) or (b) and electrochemically active only when (a) and (b) are not specifically bound. Such an electrode is useful in assay of a system which unbinds (a) and (b), at least in part, thereby to provide mediator for the enzyme/substrate reaction.

Alternatively the area of the first electrode may comprise (A) a ligand such as an antibody; (B) an antiligand such as a hapten with specific binding properties thereto; and (C) a mediator conjugated to (B) only, the ligand and antiligand remaining unbound. Such an electrode is useful in assay where antiligand in a biological fluid added to the system compete for binding sites on the ligand with the mediator conjugated antiligand already on the electrode. The resulting electrochemical activity of the electrode is a function of the amount of antiligand/mediator conjugate which remains free of the ligand.

Alternatively, the strip can be used as part of an invasive probe, as described in U.S. Ser. No. 607,599.

We claim:

1. A method of making a single use disposable electrode strip for attachment to signal readout circuitry of a sensor system to detect a current representative of a compound in a liquid sample, the strip comprising:

a) an elongated support adapted for releasable attachment to said readout circuitry;

b) a first conductor extending along said support and comprising a conductive element for connection to said readout circuitry; and c) an active electrode on said support in contact with said first conductor, said active electrode comprising, in a single printed layer on said support, an admixture of an enzyme capable of catalyzing a reaction involving a substrate for said enzyme, a conductive material, and a mediator capable of transferring electrons transferred between said enzyme-catalyzed reaction and said first conductor to create a current representative of the activity of said enzyme and representative of said compound;

the method comprising:

a) supplying an ink comprising said admixture of said enzyme, said conductive material, and said mediator; and b) printing said active electrode by applying said ink to said support in a single layer in contact with said first conductor.

2. The method of claim 1 further comprising the step of, prior to supplying the admixture, adsorbing said mediator on said conductive material.

3. The method of claim 1, wherein said step of printing said active electrode comprises screen printing said ink.

4. The method of claim 1, further comprising providing, on said elongated support at an end thereof remote from said conductive element, an area not covered by said active electrode to allow for handling of said strip.

5. The method of claim 1, further comprising the steps of positioning said conductive element for connection to readout circuitry toward one end of the support, and positioning said active electrode remote from said end.

6. The method of claim 1, further comprising the step of configuring said conductive element so as to allow releasable attachment with a socket on a readout meter.

7. The method of claim 1, further comprising the step of configuring said conductive element so as to allow releasable attachment to a resilient mounting in said socket.

8. The method of claim 1, further comprising the step of configuring said conductive element so as to allow releasable mounting with an opposed contact in said mounting.

* * * * *